(12) United States Patent
Ravishankar et al.

(10) Patent No.: US 9,011,907 B2
(45) Date of Patent: *Apr. 21, 2015

(54) COATED PHARMACEUTICAL OR NUTRACEUTICAL PREPARATION WITH ENHANCED PULSED ACTIVE SUBSTANCE RELEASE

(75) Inventors: Hema Ravishankar, Chembur (IN); Shradda Bodinge, Mumbai (IN); Hans-Ulrich Petereit, Darmstadt (DE)

(73) Assignee: Evonik Röhm GmbH, Darmstadt (DE)

( * ) Notice: Subject to any disclaimer, the term of this patent is extended or adjusted under 35 U.S.C. 154(b) by 71 days.

This patent is subject to a terminal disclaimer.

(21) Appl. No.: 12/742,945

(22) PCT Filed: Feb. 1, 2008

(86) PCT No.: PCT/EP2008/051238
§ 371 (c)(1),
(2), (4) Date: May 14, 2010

(87) PCT Pub. No.: WO2009/086941
PCT Pub. Date: Jul. 16, 2009

(65) Prior Publication Data
US 2010/0291202 A1 Nov. 18, 2010

(30) Foreign Application Priority Data
Jan. 10, 2008 (IN) .............. 96/CHE/2008

(51) Int. Cl.
*A61K 9/64* (2006.01)
*A61K 9/20* (2006.01)
*A61K 9/50* (2006.01)

(52) U.S. Cl.
CPC ............. *A61K 9/5078* (2013.01); *A61K 9/2081* (2013.01)

(58) Field of Classification Search
None
See application file for complete search history.

(56) References Cited

U.S. PATENT DOCUMENTS

| | | | |
|---|---|---|---|
| 5,395,628 A * | 3/1995 | Noda et al. .................. 424/490 |
| 6,878,387 B1 * | 4/2005 | Petereit et al. ............... 424/490 |
| 2002/0192282 A1 | 12/2002 | Beckert et al. |
| 2006/0204576 A1 | 9/2006 | Petereit et al. |
| 2006/0269605 A1 | 11/2006 | Lizio et al. |
| 2007/0042045 A1 | 2/2007 | Lizio et al. |
| 2008/0044470 A1 | 2/2008 | Petereit et al. |
| 2008/0069878 A1 | 3/2008 | Venkatesh et al. |
| 2008/0206324 A1 | 8/2008 | Gryczke et al. |
| 2008/0220080 A1 | 9/2008 | Petereit et al. |

FOREIGN PATENT DOCUMENTS

| | | |
|---|---|---|
| EP | 0 040 590 A2 | 11/1981 |
| EP | 0 386 967 A2 | 9/1990 |
| JP | 3-7238 | 1/1991 |
| JP | 3-204810 | 9/1991 |
| JP | 7-112932 | 5/1995 |
| JP | 8-143476 | 6/1996 |
| JP | 2002-526401 | 8/2002 |
| JP | 2004-536855 A | 12/2004 |
| JP | 2007-509891 A | 4/2007 |
| JP | 2007-510677 | 4/2007 |
| KR | 10-2006-0121182 | 11/2006 |
| WO | 2006 102964 | 10/2006 |
| WO | 2008/027993 | 3/2008 |

OTHER PUBLICATIONS

Wu, Chuanbin; McGinity, James W. Influence of an Enteric Polymer on Drug Release Rates of Theophylline from Pellets Coated with Eudragit RS 30D. Pharmaceutical Development and Technology, 2003, vol. 8, No. 1, p. 103-110.*
U.S. Appl. No. 60/908,854, filed Mar. 29, 2007, Gryczke, et al.
U.S. Appl. No. 12/742,842, filed May 13, 2010, Ravishankar, et al.
U.S. Appl. No. 12/742,263, filed May 11, 2010, Ravishankar, et al.
U.S. Appl. No. 12/742,945, filed May 14, 2010, Ravishankar, et al.
Office Action issued Jan. 4, 2013 in Japanese Application No. 2010-541718 (English Translation).
Office Action issued Oct. 7, 2013, in Japanese Patent Application No. 201 0-541718 (submitting English translation only).
Office Action issued Jul. 31, 2014 in Korean Patent Application No. 10-2010-7015178 filed Jan. 10, 2008 w/English translation.

* cited by examiner

*Primary Examiner* — Susan Tran
*Assistant Examiner* — Jessica Worsham
(74) *Attorney, Agent, or Firm* — Oblon, McClelland, Maier & Neustadt, L.L.P.

(57) ABSTRACT

The present invention relates to a pharmaceutical or nutraceutical preparation comprising a) a core containing a pharmaceutically or nutraceutically active substance and a substance that acts in a modulatory manner with regard of the release of pharmaceutically or nutraceutically active substances; and b) a controlling layer surrounding the core comprising i) 55 to 92% by weight based on the total weight of (meth)acrylic copolymers present in the layer of one or a mixture of a plurality of (meth)acrylate copolymers composed of 80 to 98% by weight based on the weight of the (meth)acrylic copolymer of structural units derived from $C_1$ to $C_4$ alkyl esters of (meth)acrylic acid and 2 to 20% by weight based on the weight of the (meth)acrylic copolymer of structural units derived from (meth)acrylate monomers with a quaternary ammonium group in the alkyl radical; and ii) 8 to 45% by weight based on the total weight of (meth)acrylic copolymers present in the layer of one or a mixture of a plurality of (meth)acrylate copolymers composed of more than 5 to 59% by weight based on the weight of the copolymer of structural units derived from acrylic acid or methacrylic acid and to tablets or capsules comprising same.

20 Claims, No Drawings

COATED PHARMACEUTICAL OR NUTRACEUTICAL PREPARATION WITH ENHANCED PULSED ACTIVE SUBSTANCE RELEASE

The invention relates to a new coated pharmaceutical or nutraceutical preparation resulting in an enhanced active substance release while ensuring a sigmoidal release pattern, to medicament forms containing such pharmaceutical preparation and to the use of certain copolymers comprising structural units derived from acrylic acid or methacrylic acid in a controlling layer comprising certain polymers containing cationic ammonium groups that surround a core containing a pharmaceutically or nutraceutically active substance in order to increase the release rate of the pharmaceutically or nutraceutically active substance or enable a more complete drug release from controlled release dosage forms in body fluids.

PRIOR ART

From the prior art many different approaches are known how to control the release of pharmaceutically active substances from pharmaceutical preparations. Different solutions are provided depending on where and in which time frame the pharmaceutically active substance shall be released in the digestive system when using oral application forms.

From U.S. Pat. No. 5,395,628 a controlled release pharmaceutical preparation comprising (a) a core containing a pharmaceutically active substance and an organic acid and (b) a coating film formed on the surface of the core by aqueous coating of a water-insoluble and slightly water permeable acrylic polymer containing trimethylammonium-ethyl groups is known. The effect of the structure according to the teaching of the '628 patent is that the pharmaceutically active substance is not dissolved and released until a fixed period of time lapses, but when the body fluid is gradually penetrated into the preparation and thereby the organic acid is dissolved the slightly water permeable polymer is rapidly changed to water permeable which results in a rapid solution and release of the pharmaceutically active substance.

A similar pharmaceutical preparation is known from EP-B-1 117 387.

Both teachings refer to the function of an organic acid or salt of an organic acid to make the coating more water permeable for release of the pharmaceutically active substance resulting in a lag time in the release pattern. As is, for example evident from the examples in U.S. Pat. No. 5,395,628 without the presence of the organic acid the drug release is very slow and incomplete.

Furthermore, several prior art documents are known that describe multilayer coated pharmaceutical preparations in order to adjust specific release patterns for the pharmaceutically active component.

WO 2005/046649, WO 2005/046561, WO 2006/102964 and WO 2006/102965 all relate to multiparticulate pharmaceutical preparations having a multilayer coating that permits to adjust the permeability of the film coatings by intrinsic modulations in order to achieve specific release profiles. This is achieved by a multiparticulate pharmaceutical form comprising a core, an inner controlling layer surrounding the core that comprises a substance having a modulating effect, especially salts of organic acids, which is embedded in a matrix of pharmaceutically acceptable polymers, waxes, resins and/or proteins. This inner controlling layer is surrounded by an active ingredient layer comprising the pharmaceutically active component. The pharmaceutical preparation additionally contains an outer controlling layer comprising acrylic copolymers having quaternary ammonium groups and up to 40 weight percent of further pharmaceutically usable polymers. Among a long list of suitable pharmaceutically acceptable polymers to be used as an optional component (meth)acrylate copolymers consisting of 20 to 40 weight percent of methylmethacrylate and 60 to 80 weight percent of methacrylic acid or crosslinked and/or uncrosslinked polyacrylic acid are disclosed. There is no information derivable with respect to the effect or purpose of such acid functional copolymers in the outer controlling layer. Furthermore, since these acid functional copolymers are disclosed as a possible alternative for the optional component in a long list of pharmaceutically acceptable polymers having totally different chemical or physical functionality it is evident that the selection of the acid functional copolymer has no relevance at all for the desired control of release pattern described in these prior art documents.

The object of the present invention in view of these prior art documents is to provide a pharmaceutical preparation for particulate pharmaceutical forms for oral administration having a less complex structure that enables substantially complete release of the pharmaceutically active component in a short period of time while ensuring a sigmoidal release profile.

SUMMARY OF THE INVENTION

The present inventors have surprisingly discovered that by incorporating (meth)acrylic copolymers comprising more than 5 to 59 weight percent based on the weight of the copolymers structural units derived from acrylic acid or methacrylic acid in a controlling layer comprising one or more (meth)acrylic copolymers having quaternary ammonium groups that surround a core containing a pharmaceutically or nutraceutically active substance and a substance that acts in a modulatory manner with regard of the release of pharmaceutically active substances increases the release rate of the pharmaceutically or nutraceutically active substance in the body fluids of the digestive system and results in a substantially complete release of the active substance in shortened period of time in a sigmoidal release profile.

Thus, the defined objective has been attained by a pharmaceutical or nutraceutical preparation comprising:
a) a core essentially comprising a pharmaceutically or nutraceutically active substance and a substance that acts in a modulatory manner with regard of the release of pharmaceutically or nutraceutically active substances; and
b) a controlling layer surrounding the core comprising
  i) 55 to 92% by weight based on the total weight of (meth)acrylic copolymers present in the layer of one or a mixture of a plurality of (meth)acrylate copolymers composed of 80 to 98% by weight based on the weight of the (meth)acrylic copolymer of structural units derived from $C_1$ to $C_4$ alkyl esters of (meth)acrylic acid and 2 to 20% by weight based on the weight of the (meth)acrylic copolymer of structural units derived from (meth)acrylate monomers with a quaternary ammonium group in the alkyl radical; and
  ii) 8 to 45% by weight based on the total weight of (meth)acrylic copolymers present in the layer of one or a mixture of a plurality of (meth)acrylate copolymers composed of more than 5 to 59% by weight based on the weight of the copolymer of structural units derived from acrylic acid or methacrylic acid.

PREFERRED EMBODIMENTS ACCORDING TO THE PRESENT INVENTION

Core (a)
  In the simplest case, the core can essentially comprise or can be composed of the active ingredient and a substance which acts in modulatory manner (modulator). Preferably the skilled person will add conventional pharmaceutical excipients, which are different from the modulator, that are exemplified by binders, such as cellulose and derivatives thereof, or polyvinyl pyrrolidone (PVP), humectants, disintegration promoters, lubricants, starch and derivatives thereof, polysaccharides solubilizers; or others. The core can also comprise a neutral carrier, e.g. a nonpareil. Sometimes even gelatine capsules or HPMC capsules can be used as cores to be coated.

The core (a) can comprise for example:
- pharmaceutically or nutraceutically active components in an amount of 97.5 to 2.5, preferably 80 to 5 weight percent based on the weight of the core;
- a substance which acts in modulatory manner (modulator) in an amount of 2.5 wt-% to 97.5 wt-%, preferably 5-80 wt-%, particularly preferred 10-50 wt-% based on the weight of the core;
- preferably pharmaceutical excipients, different from the modulator, which may function as binders in an amounts of 0.5 to 50, preferably 5 to 50 weight percent based on the weight of the core;
- optionally a neutral carrier, non pareil seed, with a proportion of the core weight of 0 to 95, preferably 10 to 60 weight percent.

The cores can be produced, for example by granulation and subsequently compression or direct compression, extrusion and subsequent rounding off, wet or dry granulation or direct pelletizing (e.g. on discs) or by binding of powders (powder layering) onto active ingredient-free beads (nonpareils) or active ingredient-containing particles.

The cores may be pellets with a size of 100 to 1500 μm or may be mini tablets with a size of 1500 to 5000 μm.

The cores may be homogenous or have a layered structure in which case the active ingredient is preferably located in the outer layer. The substance (in the following modulatory substance) that acts in a modulatory manner with regard of the release of pharmaceutically active substances may be present in an homogenous mixture with the pharmaceutical substance. Alternatively the modulatory substance may be integral ingredient of a layer above or beneath a layer comprising a pharmaceutically active substance within the core.

According to a preferred embodiment of the present invention the core is free of a controlling layer comprising pharmaceutically acceptable polymers, waxes, resins and/or proteins. According to this embodiment such a controlling layer is neither present beneath an active component layer, nor above an active component layer. But the core may optionally comprise sub-coating layers without release controlling functionality. Such coatings are preferably water-soluble and may be applied at very low thickness for example less than 15 μm or less than 10 μm. A suitable material for such sub-coating layers is HPMC or PVP. The function of such sub-coating layers is to avoid incompatibilities of the active ingredient with the controlling layer.

According to a preferred embodiment of the present invention an inactive carrier such as nonpareil is first loaded with the modulary substance and then with the pharmaceutically active component and optionally with pharmaceutical excipients.

Modulary Substance:

The substance that acts in a modulatory manner with regard of the release of pharmaceutically or nutraceutically active substances is a modulatory substance or a modulator. The modulatory substance employed must be toxicologically acceptable and usable in medicaments. The modulary substance may preferably have a molecular weight of less than 500. The modulary substances are preferably available in solid form and are preferably ionogenic.

The modulatory substance may be an inorganic salt like sodium chloride or potassium nitrate or chloride. Preferred modulary substances are organic acids or salts of organic acids.

The organic acids employed must be toxicologically acceptable and usable in medicaments. The preferred type depends on the specific formulation. Organic acids, such as citric acid, fumaric acid, formic acid, succinic acid, acetic acid, maleic acid, tartaric acid, glutaric acid or lactic acid are preferred. Substances which are liquid as free acids, like formic acid, acetic acid or lactic acid, are preferably applied in their solid form as salts.

Succinic acid is particularly suitable for the purposes of the invention. Citric acid is in principle likewise suitable although the release profiles obtained in buffered media which approximately correspond to physiological conditions are not so steep as with succinate. Acidic acid may occasionally lead to stability problems which may appear during storage of the pharmaceutical forms. No such problems are known as yet when succinic acid is used.

The type of modulatory substance controls the steepness of the active ingredients in the release plot, especially in sigmoidal release plots. For instance NaCl or Na-citrate are slowing down the release of the active ingredient, thus the release curves become less steep. On the other hand for instance Na-succinate, Na-acetate or citric acid are accelerating the release of the active ingredient, thus the release curves become steeper.

The amount of the organic acid(s) as a proportion of the weight of the core may be 2.5 wt-% to 97.5 wt-%, preferably 5-80 wt-%, particularly preferred 20-60 wt-%.

Salts of organic acids are preferred to the organic acids. In most cases a slower active ingredient release during the lag time and subsequently a faster active ingredient release is observed when using the organic acids and salts compared with the organic acids themselves.

The employed salts of organic acids must be toxicologically acceptable and usable in medicaments. Alkali metal salts (lithium, sodium, potassium) and ammonium salts are preferred. The preferred type depends on specific formulations. Besides the functionality according to the invention, however, the pharmacological effects of the ions must also be taken into account. Salts of weak organic acids, such as succinic acid, citric acid, fumaric acid, formic acid, acetic acid, maleic acid, tartaric acid, glutaric acid, or lactic acid are preferred. Sodium succinate is particularly suitable for the purpose of the invention. Sodium citrate is in principle likewise suitable although the release profiles obtained in buffered media which approximately correspond to physiological conditions are not so steep as with sodium succinate. Sodium acetate may occasionally lead to stability problems which may appear during storage of the pharmaceutical form which are not known from sodium succinate.

The type of acid in the salt controls the steepness of the active ingredient release plot, especially in sigmoidal release plots.

The amount of the salts of the organic acids as a proportion of the weight of the core may be 2.5 wt-% to 97.5 wt-%, preferably 5-80 wt-%, in particular 20-60 wt-%.

Controlling Layer (b):

The controlling layer (b) contains a combination of cationic (meth)acrylic copolymers and (meth)acrylic copolymers having anionic groups and/or groups convertible to anionic groups, and optionally conventional pharmaceutical excipients such as, for example plasticizers, pigments, wetting agents, etc. The controlling layer (b) preferably envelops the core directly without further layers being present between the core and the coating layer. Especially no further controlling layer comprising pharmaceutically acceptable polymers, waxes, resins and/or proteins is positioned between the core (a) and the controlling layer (b). The polymers in the controlling coating (b) are of a film forming type and the coating is converted to a film together with the optionally present excipients to form a continuous coating or coating film. The coating or coating film in its entirety controls the release of the pharmaceutically active component.

The controlling layer (b) according to the present invention comprises:

i) 55 to 92 weight percent based on the total weight of (meth) acrylic copolymers present in the layer of one or a mixture of a plurality of (meth)acrylate copolymers composed of 80 to 98 weight percent based on the weight of the (meth) acrylic copolymer of structural units derived from $C_1$ to $C_4$ alkyl esters of (meth)acrylic acid and 2 to 20 weight percent based on the weight of the (meth)acrylic copolymer of structural units derived from (meth)acrylate monomers with a quaternary ammonium group in the alkyl radical; and ii) 8 to 45 weight percent based on the total weight of (meth) acrylic copolymers present in the layer of one or a mixture of a plurality of (meth)acrylate copolymers composed of more than 5 to 59 weight percent based on the weight of the copolymer of structural units derived from acrylic acid or methacrylic acid.

Component i)—(Meth)Acrylic Copolymer Containing Quaternary Ammonium Groups

According to one embodiment of the present invention the copolymers according to component i) comprise (meth)acrylate copolymers composed of 80 to 98 weight percent based on the weight of the (meth)acrylic copolymer of structural units derived from $C_1$ to $C_4$ alkyl esters of (meth)acrylic acid and 2 to 20 weight percent based on the weight of the (meth) acrylic copolymer of structural units derived from (meth) acrylate monomers with a quaternary ammonium group in the alkyl radical. The structural units containing a quaternary ammonium group in the alkyl radical that are present in the copolymer according to component i) of the present invention are preferably derived from 2-trimethylammonium ethylmethacrylate chloride.

According to one embodiment of the present invention the copolymers according to component i) comprise (meth)acrylate copolymers composed of 93 to 98 weight percent based on the weight of the (meth)acrylic copolymer of structural units derived from $C_1$ to $C_4$ alkyl esters of (meth)acrylic acid and 2 to 7 weight percent based on the weight of the (meth) acrylic copolymer of structural units derived from (meth) acrylate monomers with a quaternary ammonium group in the alkyl radical (EUDRAGIT® RS-type).

One preferred copolymer to be used as component i) is composed, for example of 50 to 70 weight percent of structural units derived from methylmethacrylate, 20 to 40 weight percent of structural units derived from ethylacrylate and 7 to 2 weight percent of trimethylammonium ethylmethacrylate. A particularly preferred copolymer comprises 65 weight percent of structural units derived from methylmethacrylate, 30 weight percent of structural units of ethylacrylate and 5 weight percent of structural units derived from 2-trimethylammonium ethylmethacrylate chloride. Such copolymers are commercially available as EUDRAGIT® RS.

Another suitable (meth)acrylate copolymer for component i) may be composed, for example of free radically polymerized monomer units of 80 to less than 93 weight percent of $C_1$ to $C_4$ alkyl esters of acrylic or (meth)acrylic acid and more than 7 to 20 weight percent of (meth)acrylate monomers having a quaternary ammonium group in the alkyl radical, preferably 85 to less than 93 weight percent of $C_1$ to $C_4$ alkyl esters of acrylic or (meth)acrylic acid and more than 7 to 15 weight percent of (meth)acrylate monomers having a quaternary ammonium group in the alkyl radical. Such (meth)acrylate copolymers are commercially available and have been used for a long time for release slowing coatings (EUDRAGIT® RL-type).

A specifically suitable copolymer comprises, for example 60 weight percent methylmethacrylate, 30 weight percent ethylacrylate and 10 weight percent of 2-trimethylammonium ethylmethacrylate chloride (EUDRAGIT® RL).

According to a particularly preferred embodiment of the present invention the copolymers according to component i) comprise a mixture of 40 to 99 weight percent based on the total weight of the mixture of (meth)acrylate copolymers composed of 93 to 98 weight percent based on the weight of the (meth) acrylic copolymer of structural units derived from $C_1$ to $C_4$ alkyl esters of (meth)acrylic acid and 2 to 7 weight percent based on the weight of the (meth)acrylic copolymer of structural units derived from (meth)acrylate monomers with a quaternary ammonium group in the alkyl radical; and 1 to 60 weight percent based on the total weight of the mixture of (meth)acrylate copolymers composed of 85 to less than 93 weight percent based on the weight of the (meth)acrylic copolymer of structural units derived from $C_1$ to $C_4$ alkyl esters of (meth)acrylic acid and more than 7 to 15 weight percent based on the weight of the (meth)acrylic copolymer of structural units derived from (meth)acrylate monomers with a quaternary ammonium group in the alkyl radical.

In the mixture the first component as defined above may be selected from the EUDRAGIT® RS-type copolymers including the preferred embodiment as defined above. The proportion of the EUDRAGIT® RS-type copolymers is 40-99, preferably 60 to 95 weight percent based on the total weight of the mixture of (meth)acrylate copolymers according to component i). Particularly preferred is a range of 70 to 90 weight percent.

A suitable (meth)acrylate copolymer for the second component of the mixture may be selected from (meth)acrylate copolymers of the EUDRAGIT® RL-type as described above. The proportion in the mixture can be up to 60 weight percent, preferably 5 to 40 weight percent, more preferred 10 to 30 weight percent based on the total amount of (meth) acrylic copolymers having quaternary ammonium groups.

Component ii)—(Meth)Acrylic Copolymer Containing Structural Units Derived from Acrylic Acid or Methacrylic Acid.

Furthermore, the controlling layer (b) comprises 8 to 45 weight percent based on the total weight of (meth)acrylic polymers present in the controlling layer (b) of one or a mixture of a plurality of (meth)acrylate copolymers composed of more than 5 to 59 weight percent based on the weight of the copolymer of structural units derived from acrylic acid or methacrylic acid.

According to a preferred embodiment in the copolymers according to component ii) the lower limit for the range of amount of structural units derived from acrylic acid or methacrylic acid is selected from at least 7 weight percent, preferably more than 15 weight percent, more preferred at least 18 weight percent based on the weight of the copolymer. According to one embodiment of the present invention the copolymers according to component ii) are composed of 40 to 59 weight percent based on the weight of the copolymer of structural units derived from acrylic acid or methacrylic acid.

The structural units derived from acrylic acid or methacrylic acid may be partially or fully neutralized for instance by alkali or ammonia ions.

Depending on the degree of neutralization of acid functional (meth)acrylic copolymer the carboxylic groups are fully or partially converted to the anionic carboxylate group.

Preferably the degree of partially neutralization is not more than 25 mol-%, not more than 12 mol-%, not more than 10 mol-%, not more than 8 mol-%. It is most preferred if the structural units derived from acrylic acid or methacrylic acid that they are not neutralized.

Preferably the copolymers according to component ii) are composed of 41 to less than 95 weight percent based on the weight of the copolymer of structural units derived from $C_1$ to $C_4$ alkyl esters of (meth)acrylic acid. Suitable upper limits for the amount of structural units derived from $C_1$ to $C_4$ alkyl esters of (meth)acrylic acid in the copolymer are selected from 93 weight percent, preferably less than 85 weight percent, more preferred 82 weight percent based on the weight of the copolymer.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

The proportions mentioned normally add up to 100% by weight. However it is also possible in addition, without this leading to an impairment or alteration of the essential properties, for small amounts in the region of 0 to 10, for example 1 to 5, % by weight of further monomers capable of vinylic copolymerization, such as, for example, hydroxyethyl methacrylate or hydroxyethyl acrylate, vinylpyrrolidone, vinylmalonic acid, styrene, vinyl alcohol, vinyl acetate and/or derivatives thereof, to be present. It is preferred that no further monomers capable of vinylic copolymerization are present.

According to a particularly preferred embodiment the component ii) of the controlling layer (b) is composed of 41 to 60 weight percent based on the weight of the copolymer of structural units derived from methylmethacrylate or ethylacrylate and 40 to 59 weight percent based on the weight of the copolymer of structural units derived from (meth)acrylic acid whereby the carboxyl functional groups on the copolymer can be fully or partially neutralized.

Following examples of (meth)acrylic copolymers are suitable as component ii) in the controlling layer (b).

EUDRAGIT® L is a copolymer of 50% by weight methyl methacrylate and 50% by weight methacrylic acid. The pH of the start of the specific active ingredient release in intestinal juice or simulated intestinal fluid can be stated to be pH 6.0.

EUDRAGIT® L 100-55 is a copolymer of 50% by weight ethyl acrylate and 50% by weight methacrylic acid. EUDRAGIT® L 30 D-55 is a dispersion comprising 30% by weight EUDRAGIT® L 100-55. The pH of the start of the specific active ingredient release in intestinal juice or simulated intestinal fluid can be stated to be pH 5.5.

Likewise suitable are anionic (meth)acrylate copolymers composed of 20 to 40% by weight methacrylic acid and 80 to 60% by weight methyl methacrylate (EUDRAGIT® S type). The pH of the start of the specific active ingredient release in intestinal juice or simulated intestinal fluid can be stated to be pH 7.0.

Suitable (meth)acrylate copolymers are those consisting of 10 to 30% by weight methyl methacrylate, 50 to 70% by weight methyl acrylate and 5 to 15% by weight methacrylic acid (EUDRAGIT® FS type). The pH at the start of the specific active ingredient release in intestinal juice or simulated intestinal fluid can be stated to be pH 7.0.

EUDRAGIT® FS is a copolymer of 25% by weight methyl methacrylate, 65% by weight methyl acrylate and 10% by weight methacrylic acid. EUDRAGIT® FS 30 D is a dispersion comprising 30% by weight EUDRAGIT® FS.

Additionally suitable is a copolymer composed of
20 to 34% by weight methacrylic acid and/or acrylic acid,
20 to 69% by weight methyl acrylate and
0 to 40% by weight ethyl acrylate and/or where appropriate
0 to 10% by weight further monomers capable of vinylic copolymerization,
with the proviso that the glass transition temperature of the copolymer according to ISO 11357-2, subsection 3.3.3, is not more than 60° C. This (meth)acrylate copolymer is particularly suitable, because of its good elongation at break properties, for compressing pellets to tablets.

Additionally suitable is a copolymer composed of
20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate 0 to 10% by weight further monomers capable of vinylic copolymerization, where the proportions of the monomers add up to 100% by weight,
with the proviso that the glass transition temperature of the copolymer according to ISO 11357-2, subsection 3.3.3 (midpoint temperature $T_{mg}$), is 55 to 70° C. Copolymers of this type are particularly suitable, because of its good mechanical properties, for compressing pellets to tablets.

The abovementioned copolymer is composed in particular of free-radical polymerized units of
20 to 33, preferably 25 to 32, particularly preferably 28 to 31% by weight methacrylic acid or acrylic acid, with preference for methacrylic acid,
5 to 30, preferably 10 to 28, particularly preferably 15 to 25% by weight methyl acrylate,
20 to 40, preferably 25 to 35, particularly preferably 18 to 22% by weight ethyl acrylate, and
more than 10 to 30, preferably 15 to 25, particularly preferably 18 to 22% by weight butyl methacrylate,
where the monomer composition is chosen so that the glass transition temperature of the copolymer is from 55 to 70° C., preferably 59 to 66, particularly preferably 60 to 65° C.

Glass transition temperature means in this connection in particular the midpoint temperature $T_{mg}$ according to ISO 11357-2, subsection 3.3.3. Measurement takes place without added plasticizer, with residual monomer contents (REMO) of less than 100 ppm, with a heating rate of 10° C./min and under a nitrogen atmosphere.

The anionic (meth)acrylate copolymers can be prepared in a manner known per se by free-radical polymerization of the monomers (see, for example, EP 0 704 207 A2 and EP 0 704 208 A2). The copolymer according to the invention can be prepared in a manner known per se by free-radical emulsion polymerization in aqueous phase in the presence of, preferably, anionic emulsifiers, for example by the process described in DE-C 2 135 073.

The copolymer can be prepared by conventional processes of free-radical polymerization continuously or discontinuously (batch processes) in the presence of free-radical forming initiators and, where appropriate, regulators to adjust the molecular weight undiluted, in solution, by bead polymerization or in emulsion. The average molecular weight Mw (weight average, determined for example by measuring the solution viscosity) may be for example in the range from 80 000 to 1 000 000 (g/mol). Emulsion polymerization in aqueous phase in the presence of water-soluble initiators and (preferably anionic) emulsifiers is preferred.

In the case of bulk polymerization, the copolymer can be obtained in solid form by crushing, extrusion, granulation or hot cut.

The (meth)acrylate copolymers are obtained in a manner known per se by free-radical bulk, solution, bead or emulsion polymerization. They must before processing be brought to the particle size range of the invention by suitable grinding, drying or spraying processes. This can take place by simple crushing of extruded and cooled pellets or hot cut.

The use of powders may be advantageous especially on mixture with other powders or liquids. Suitable apparatuses for producing powders are familiar to the skilled person, e.g. air jet mills, pinned disc mills, compartment mills. It is possible where appropriate to include appropriate sieving steps. A suitable mill for industrial large quantities is, for example, an opposed jet mill (Multi No. 4200) operated with a gauge pressure of about 6 bar.

Bases suitable for the at least partial neutralization of the anionic (meth)acrylic copolymers of the invention are those expressly mentioned in EP 0 088 951 A2 or WO 2004/096185 or derivable therefrom. The following bases are suitable in particular: sodium hydroxide solution, potassium hydroxide solution (KOH), ammonium hydroxide or organic bases such as, for example, triethanolamine, sodium carbonate, potassium carbonate, sodium bicarbonate, trisodium phosphate, trisodium citrate or ammonia or physiologically tolerated amines such as triethanolamine or tris(hydroxymethyl)aminomethane.

Further suitable cationic, organic bases are basic amino acids histidine, arginine and/or lysine.

Further Pharmaceutically Usual Excipients

The core and/or the coating may comprise further pharmaceutically usual excipients. Further additives, in particular as processing aids, are intended to ensure a reliable and reproducible production process and good long-term storage stability. They may influence the permeability of the coatings which can be utilized where appropriate as additional control parameters. As discussed above the pharmaceutical excipients which may be present in the core in addition to the pharmaceutically active component may be, for example binders, such as cellulose and derivatives thereof, polyvinyl pyrrolidone (PVP), gelatin, (meth)acrylates, starch and derivatives thereof, or sugars.

—Plasticizers:

Plasticizers may be present, in particular in the coating or in the (meth)acrylic copolymers of the coating. Substances suitable as plasticizers usually have a molecular weight of between 100 and 20,000 and comprise one or more hydrophilic groups in the molecule, e.g. hydroxyl, ester or ammonium groups. They are frequently esters which are liquid at room temperature, such as citrates, phthalates, sebacates or castor oil. Examples of suitable plasticizers are alkyl citrates, e.g. triethyl citrate, glycerol esters, alkyl phthalates, alkyl sebacates, sucrose esters, sorbitan esters, diethyl sebacate, dibutyl sebacate and polyethylene glycols with a molecular weight of 4,000 to 20,000. Preferred plasticizers are triethyl citrate and acetyl triethyl citrate. The plasticizers may be present, for example in amounts of from 5 to 25 weight percent based on the polymers of the coating.

—Non-Sticking Agents:

These substances which usually have lipophilic properties, can be added to the spray suspensions and prevent agglomeration of the cores during the film coating. It is possible to employ, for example talc, silica, kaolin, magnesium stearate or calcium stearate or non-ionic emulsifiers with an HLB of between 3 and 8, like glycerol monostearate. The usual amounts employed are between 0.5 to 100 weight percent based on the weight of the cores. The non-sticking agents may alternatively employed in the coating, preferably in an amount of 0.5 to 100 weight percent based on the total weight of the polymers in the coating.

—Further Excipients:

Further pharmaceutically usual excipients which can be added in a manner known per se are, for example, pharmaceutically acceptable stabilizers, colorants, antioxidants, wetting agents, pore formers, pigments, gloss agents, etc.

Pharmaceutically Active Components

The multilayer pharmaceutical form of the invention is suitable in principle for any pharmaceutically active components. Medicinal substances in use can be found in reference works such as, for example, the Rote Liste or the Merck Index.

The active components or medicinal substances employed for the purposes of the invention are intended to be used on or in the human or animal body in order
1. to cure, to alleviate, to prevent or to diagnose disorders, conditions, physical damage or pathological symptoms;
2. to reveal the condition, the status or the functions of the body or mental states;
3. to replace active substances or body fluids produced by the human or animal body;
4. to ward off, to eliminate or to render harmless pathogens, parasites or exogenous substances, or
5. to influence the condition, the status or the functions of the body or mental states.

These pharmaceutically active substances may belong to one or more active ingredient classes such as ACE inhibitors, adrenergics, adrenocorticosteroids, acne therapeutic agents, aldose reductase inhibitors, aldosterone antagonists, alpha-glucosidase inhibitors, alpha 1 antagonists, remedies for alcohol abuse, amino acids, amoebicides, anabolics, analeptics, anaesthetic additions, anaesthetics (non-inhalational), anaesthetics (local), analgesics, androgens, angina therapeutic agents, antagonists, antiallergics, antiallergics such as PDE inhibitors, antiallergics for asthma treatment, further antiallergics (e.g. leukotriene antagonists, antianaemics, antiandrogens, antianxiolytics, antiarthritics, antiarrhythmics, antiatheriosclerotics, antibiotics, anticholinergics, anticonvulsants, antidepressants, antidiabetics, antidiarrhoeals, antidiuretics, antidotes, antiemetics, antiepileptics, antifibrinolytics, antiepileptics, antihelmintics, antihistamines, anti hypotensives, antihypertensives, antihypertensives, antihypotensives, anticoagulants, antimycotics, antiestrogens, antiestrogens (non-steroidal), antiparkinson agents, antiinflammatory agents, antiproliferative active ingredients, antiprotozoal active ingredients, antirheumatics, antischistosomicides, antispasmolytics, antithrombotics, antitussives, appetite suppressants, arteriosclerosis remedies, bacteriostatics, beta-blockers, beta-receptor blockers, bronchodilators, carbonic anhydrase inhibitors, chemotherapeutic agents, choleretics, cholinergics, cholinergic agonists, cholinesterase inhibitors, agents for the treatment of ulcerative colitis, cyclooxygenaze inhibitors diuretics, ectoparasiticides, emetics, enzymes, enzyme inhibitors, enzyme inhibitors, active ingredients to counter vomiting, fibrinolytics, fungistatics, gout remedies, glaucoma therapeutic agents, glucocorticoids, glucocorticosteroids, haemostatics, cardiac glycosides, histamine H2 antagonists, hormones and their inhibitors, immunotherapeutic agents, cardiotonics, coccidiostats, laxatives, lipid-lowering agents, gastrointestinal therapeutic agents, malaria therapeutic agents, migraine remedies, microbiocides, Crohn's disease, metastasis inhibitors, migraine remedies, mineral preparations, motility-increasing active ingredients, muscle relaxants, neuroleptics, active ingredients for treatment of estrogens, osteoporosis, otologicals, antiparkinson agents, phytopharmaceuticals, proton pump inhibitors, prostaglandins, active ingredients for treating benign prostate hyperblasia, active ingredients for treating pruritus, psoriasis active ingredients, psychoactive drugs, free-radical scavengers, renin antagonists, thyroid therapeutic agents, active ingredients for treating seborrhoea, active ingredients to counter seasickness, spasmolytics, alpha- and beta-sympathomimetics, platelet aggregation inhibitors, tranquilizers, ulcer therapeutic agents, further ulcer therapeutic agents, agents for the treatment of urolithiasis, virustatics, vitamins, cytokines, active ingredients for combination therapy with cytostatics, cytostatics.

Examples of suitable active components are acarbose, acetylsalicylic acid, abacavir, aceclofenac, aclarubicin, acyclovir, actinomycin, adalimumab, adefovir, adefovirdipivoxil, adenosylmethionine, adrenaline and adrenaline derivatives, agalsidase alpha, agalsidase beta, alemtuzumab, almotriptan, alphacept, allopurinol, almotriptan, alosetron, alprostadil, amantadine, ambroxol, amisulpride, amlodipine, amoxicillin, 5-aminosalicylic acid, amitriptyline, amlodipine, amoxicillin, amprenavir, anakinra, anastrozole, androgen and androgen derivatives, apomorphine, aripiprazole, arsenic trioxide, artemether, atenolol, atorvastatin, atosiban, azathioprine, azelaic acid, barbituric acid derivatives, balsalazide, basiliximab, beclapermin, beclomethasone, bemiparin, benzodiazepines, betahistine, bexaroten, bezafibrate, bicalutamide, bimatoprost, bosentan, botulinus toxim, brimonidine, brinzolamide, budesonide, budipine, bufexamac, bumetanide, buprenorphine, bupropion, butizine, calcitonin, calcium antagonists, calcium salts, candesartan, capecitabine, captopril, carbamazepine, carifenacin, carvedilol, caspofungin, cefaclor, cefadroxil, cefalexin cefalosporins, cefditoren, cefprozil, celecoxib, cepecitabine, cerivastatim, cetirizine, cetrorelix, cetuximab, chenodeoxycholic acid, chorionic gonadotropin, ciclosporin, cidofovir, cimetidine, ciprofloxacin, cisplatin, cladribine, clarithromycin, clavulanic acid, clindamycin, clobutinol, clonidine, clopidogrel, codeine, caffeine, colestyramine, cromoglicic acid, cotrimoxazole, coumarin and coumarin derivatives, darbepoetin, cysteamine, cysteine, cytarabine, cyclophosphamide, cyproterone, cytarabine, daclizumab, dalfopristin, danaparoid, dapiprazole, darbepoetin, defepripone, desipramine, desirudin, desloaratadine, desmopressin, desogestrel, desonide, dexibuprofen, dexketoprofen, disoproxil, diazepam and diazepam derivatives, dihydralazine, diltiazem, dimenhydrinate, dimethyl sulphoxide, dimeticon, dipivoxil, dipyridarnoi, dolasetron, domperidone, and domperidane derivatives, donepzil, dopamine, doxazosin, doxorubizin, doxylamine, diclofenac, divalproex, dronabinol, drospirenone, drotrecogin alpha, dutasteride, ebastine, econazole, efavirenz, eletripan, emidastine, emtricitabine, enalapril, encepur, entacapone, enfurvirtide, ephedrine, epinephrine, eplerenone, epoetin and epoetin derivatives, eprosartan, eptifibatide, ertapenem, esomeprazole, estrogen and estrogen derivatives, etanercept, ethenzamide, ethinestradiol, etofenamate, etofibrate, etofylline, etonogestrel, etoposide, exemestan, exetimib, famciclovir, famotidine, faropenan daloxate, felodipine, fenofibrate, fentanyl, fenticonazole, fexofenadine, finasteride, fluconazole, fludarabine, flunarizine, fluorouracil, fluoxetine, flurbiprofen, flupirtine, flutamide, fluvastatin, follitropin, fomivirsen, fondaparinux, formoterol, fosfomicin, frovatriptan, furosemide, fusidic acid, gadobenate, galantamine, gallopamil, ganciclovir, ganirelix, gatifloxacin, gefitinib, gemfibrozil, gentamicin, gepirone, progestogen and progestogen derivatives, ginkgo, glatiramer, glibenclamide, glipizide, glucagon, glucitol and glucitol derivatives, glucosamine and glucosamine derivatives, glycoside antibiotics, glutathione, glycerol and glycerol derivatives, hypothalamus hormones, goserelin, grepafloxacin, gyrase inhibitors, guanethidine, gyrase inhibitors, haemin, halofantrine, haloperidol, urea derivatives as oral antidiabetics, heparin and heparin derivatives, cardiac glycosides, hyaluronic acid, hydralazine, hydrochlorothiazide and hydrochlorothiazide derivatives, hydroxyomeprazole, hydroxyzine, ibritumomab, ibuprofen, idarubicin, ifliximab, ifosfamide, iloprost, imatinib, imidapril, imiglucerase, imipramine, imiquimod, imidapril, indometacin, indoramine, infliximab, insulin, insulin glargin, interferons, irbesartan, irinotecan, isoconazole, isoprenaline, itraconazole, ivabradines, iodine and iodine derivatives, St. John's wort, potassium salts, ketoconazole, ketoprofen, ketotifen, lacidipine, lansoprazole, laronidase, latanoprost, leflunomide, lepirudin, lercanidipine, leteprinim, letrozole, levacetylmethadol, levetiracetam, levocetirizine, levodopa, levodrpropicin, levomethadone, licofelone, linezolide, lipinavir, lipoic acid and lipoic acid derivatives, lisinopril, lisuride, lofepramine, lodoxamide, lomefloxacin, lomustine, loperamide, lopinavir, loratadine, lornoxicam, losartan, lumefantrine, lutropine, magnesium salts, macrolide antibiotics, mangafodipir, maprotiline, mebendazole, mebeverine, meclozine, mefenamic acid, mefloquine, meloxicam, memantine, mepindolol, meprobamate, meropenem, mesalazine, mesuximide, metamizole, metformin, methadone, methotrexate, methyl 5-amino-4-oxopentanoate, methylnaloxone, methylnaloxone, methylnaltrexones, methylphenidate, methylprednisolone, metixen, metoclopramide, metoprolol, metronidazole, mianserin, mibefradil, miconazole, mifepristone, miglitol, miglustad, minocycline, minoxidil, misoprostol, mitomycin, mizolastine, modafinil, moexipril, montelukast, moroctocog, morphinans, morphine and morphine derivatives, moxifloxacin, ergot alkaloids, nalbuphine, naloxone, naproxen, naratriptan, narcotine, natamycin, nateglinide, nebivolol, nefazodone, nelfinavir, neostigmine, neramexan, nevirapine, nicergoline, nicethamide, nifedipine, niflumic acid, nimodipine, nimorazole, nimustine, nesiritide, nisoldipine, norfloxacin, novamine sulphone, noscapine, nystatin, ofloxacin, oktotride, olanzapine, olmesartan, olsalazine, oseltamivir, omeprazole, omoconazole, ondansetron, orlistat, oseltamivir, oxaceprol, oxacillin, oxaliplatin, oxaprozin, oxcarbacepin, oxicodone, oxiconazole, oxymetazoline, palivizumab, palanosetron, pantoprazole, paracetamol, parecoxib, paroxetine, pegaspargase, peginterferon, pegfilgrastrim, penciclovir, oral penicillins, pentazocine, pentifylline, pentoxifylline, peptide antibiotics, perindopril, perphenazine, pethidine, plant extracts, phenazone, pheniramine, phenylbutyric acid, phenyloin, phenothiazines, phenserine, phenylbutazone, phenyloin, pimecrolimus, pimozide, pindolol, pioglitazone, piperazine, piracetam, pirenzepine, piribedil, pirlindol, piroxicam, pramipexol, pramlintide, pravastatin, prazosin, procaine, promazine, propiverine, propranolol, propionic acid derivatives, propyphenazone, prostaglandins, protionamide, proxyphylline, quetiapine, quinapril, quinaprilate, quinupristine, ramipril, ranitidine, rabeprazole, raloxifen, ranolazine, rasburicase, reboxetin, repaclinides, reproterol, reserpine, revofloxacin, ribavirin, rifampicin, riluzoles, rimexolone, risedronate, risperidone, ritonavir, rituximab, rivastimen, risatriptan, rofecoxib, ropinirol, ropivacaine, rosiglitazone, roxatidine, roxithromycin, ruscogenin, rosuvastatin, rutoside and rutoside derivatives, sabadilla, salbutamol, salicylates, salmeterol, saperconazoles, thyroid hormones, scopolamine, selegiline, sertaconazole, sertindole, sertraline, sevelamer, sibutramine, sildenafil, silicates, simvastatin, sirolimus, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulphasalazine, sulpiride, sultamicillin, sultiam, sumatriptan, suxamethonium chloride, tacrine, tacrolimus, tadalafil, taliolol, talsaclidine, tamoxifen, tasonermin, tazarotene, tegafur, tegaserod, telithromycin, telmisartan, temoporfin, temozolomide, tenatoprazole, tenecteplase, teniposide, tenofovir, tenoxicam, teriparatide, terazosin, terbinafine, terbutaline, terfenadine, teriparatide, terlipressin, tertatolol, testosterone and testosterone derivatives, tetracyclines, tetryzoline, tezosentan, theobromine, theophylline, theophylline derivatives, thiamazole, thiotepa, thr. growth factors, tiagabine, tiapride, tibolone, ticlopidine, tilidine, timolol, timidazole, tioconazole, tioguanine, tiotropium, tioxolone, tirazetam, tiropramide, trofiban, tizanidine, tolazoline, tolbutamide, tolcapone, tolnaftate, tolperisone, tolterodine, topiramate, topotecan, torasemide, tramadol, tramazoline, trandolapril, tranylcypromine, trapidil, trastuzumab, travoprost, trazodone, trepostinil, triamcinolone and triamcinolone derivatives, triamterene, trifluperidol, trifluridine, trimetazidines, trimethoprim, trimipramine, tripelennamine, triprolidine, trifosfamide, tromantadine, trometamol, tropalpine, trovafloxacin, troxerutin, tulobuterol, trypsins, tyramine, tyrothricin, urapidil, ursodeoxycholic acid, theophylline ursodeoxycholic acid, valaciclovir, valdecoxib, valganciclovir, valproic acid, valsartan, vancomycin, vardenafil, vecuronium chloride, venlafaxine, verapamil, verteporfin, vidarabine, vigabatrine, viloxazine, vinblastine, vincamine, vincristine, vindesine, vinorelbine, vinpocetine, viquidil, vitamin D and derivatives of vitamin D, voriconazole, warfarin, xantinol nicotinate, ximelagatran, xipamide, zafirlukast, zalcitabine, zaleplon, zanamivir, zidovudine, ziprasidone, zoledronic acid, zolmitriptan, zolpidem, zoplicone, zotepine and the like.

The active components can, if desired, also be used in the form of their pharmaceutically acceptable salts or derivatives, and in the case of chiral active ingredients it is possible to employ both optically active isomers and racemates or mixtures of diastereomers. If desired, the compositions of the invention may also comprise two or more active pharmaceutical ingredients.

Nutraceuticals

Nutraceuticals can be defined as extracts of foods claimed to have medical effects on human health. The nutraceutical is usual contained in a medical format such as capsule, tablet or powder in a prescribed dose. Examples for nutraceuticals are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flavonoids, antioxidants, alpha-linoleic acid from flax seed, beta-carotene from marigold petals or antocyanins from berries. Sometimes the expression neutraceuticals is used as synonym for nutraceuticals.

Application of the Controlling Layer (b):

The application process may be selected from spray application from organic solutions or aqueous dispersions, or melting or direct powder application. It is essential for implementation in this case that a uniform pore-free coating is produced. Although application of aqueous dispersions is preferred compared to organic solutions, especially in countries where strict VOC requirements have to be met, it is also possible to apply the coating application by using an organic solution.

Suitable application processes can be found, for example, in Bauer, K. H., Lehmann, K., Osterwald, H. P. Rothgang, G. "Coated Pharmaceutical Dosage Forms", 1998, Wissenschaftliche Verlagsgesellschaft mbH, Stuttgart and CRC Press LLC, Boca Raton, Fla., USA or McGinity, J. W., "Aqueous Polymeric Coatings for Pharmaceutical Dosage Forms, Second Edition, Revised and Expanded", 1997, Marcel Dekker Inc., New York, USA.

Relevant properties, required tests and specifications for the application are listed in pharmacopoeias.

Details are to be found in customary textbooks, e.g.:

Voigt, R. (1984), Lehrbuch der pharmazeutischen Technologie; Verlag Chemie Weinheim—Beerfield Beach/Fla.—Basle.

Sucker, H., Fuchs, P., Speiser, P.: Pharmazeutische Technologie, Georg Thieme Verlag Stuttgart (1991), especially Chapters 15 and 16, pp. 626-642.

Gennaro, A., R. (Editor), Remington's Pharmaceutical Sciences, Mack Publishing Co., Easton Pa. (1985), Chapter 88, pp. 1567-1573.

List, P. H. (1982): Arzneiformenlehre, Wissenschaftliche Verlagsgesellschaft mbH, Stuttgart.

The controlling layer (b) is preferably applied to the core in an amount to result in a total weight of controlling layer (b) from 2.5 to 100, preferably 10 to 70, particularly preferred 15 to 40 weight percent based on the total weight of core (a).

Topcoats

The pharmaceutical or nutraceutical preparation of the present invention may optionally comprise a topcoat that does not have any release controlling functionality. Preferably the topcoat is a water-soluble layer that functions as carrier for pigments or lubricants. A suitable topcoat material may be selected from polysaccharides.

Administration Forms

It is in principle possible for the pharmaceutical or nutraceutical preparations according to the present invention to be used directly by oral administration. However, further processing steps preferably follow in a manner known for producing pharmaceutical forms. The preparation may be present, for example in colored form which can be processed by means of pharmaceutically usual excipients, and in a manner known per se to multiparticulate pharmaceutical forms, in particular to pellet containing tablets, mini-tablets, capsules, sachets or reconstitutable powders.

The preparation according to the present invention can preferably be compressed in the form of pellets, for example to give a tablet. Alternatively the preparation can, for example also be in the form of pellets or mini-tablets which are introduced into a gelatin capsule or HPMC (Methylose) capsule and enveloped thereby.

EXAMPLES

The following copolymers were used in the Examples.
Copolymer 1:
Obtained from 65 weight percent of methyl methacrylate, 30 weight percent of ethyl acrylate and 5 weight percent 2-trimethylammoniumethyl methacrylate chloride (EUDRAGIT® RS).
Copolymer 2:
Obtained from 60 weight percent of methyl methacrylate, 30 weight percent of ethyl acrylate and 10 weight percent 2-trimethylammoniumethyl methacrylate chloride (EUDRAGIT® RL).

Copolymer 3:
Obtained from 50 weight percent of methyl methacrylate and 50 weight percent methacrylic acid (EUDRAGIT® L) used without neutralization.

Copolymer 4:
Obtained from 70 weight percent of methyl methacrylate and 30 weight percent methacrylic acid (EUDRAGIT® S) used without neutralization.

Methods

Model Drug
Studies were conducted using Phenylephrine hydrochloride as a model drug.

Excipients
All excipients were used in pharmaceutical quality

Dissolution Studies
Coated pellets were tested according to
USP 28-NF23, General Chapter <711>, Dissolution, Dissolution Parameters:
Apparatus: USP Type-I (Basket)
RPM: 100/min.
Temperature: 37.5±0.5° C.
Dissolution volume: 900 ml.
Withdrawal volume: 5 ml withdrawn manually using pipette, without replenishment of the medium.
Withdrawal interval: initial, 1.0 Hr, 2.0 Hr, 3.0 Hr, 4.0 Hr, 5.0 Hr, 6.0 Hr, 6.5 Hr, 7.0 Hr, 7.5 Hr 8.0 Hr, 9.0 Hr, 10.0 Hr, 11.0 Hr and 12.0 Hr.

Mode of detection: HPLC

Dissolution Medium 1:
0.1 molar Hydrochloric acid (HCl), (European Pharmacopoeia=EP)

Dissolution Medium 2:
Buffer pH 4.5 (United States Pharmacopoeia=USP)

Dissolution Medium 3:
Phosphate buffer pH 7.4 (United States Pharmacopoeia=USP)

Formulation Details
Cores (sugar sphere etc.) of 355-500 microns were loaded with Phenylephrine hydrochloride in a fluidised bed processor using bottom spray. Polyvinyl pyrrolidone was used as a binder.

Preparation of Pharmaceutical Preparations

In a first step the non pareil seeds were loaded with sodium succinate hexahydrate and thereafter with phenylepherine hydrochloride and the excipients for the core as cited in Table 1. A coating composition was prepared using two different concentrations of copolymer 3 or copolymer 4, whereby copolymer 3 or 4 was dispersed as a fine powder in aqueous coating solution containing a mixture of copolymer 1 and copolymer 2 in the relative amounts shown in Table 1.

Coating Suspension Preparation:
EUDRAGIT® dispersions are mixed in a suitable vessel applying gentle stirring. Lubricants and different exipients are dissolved or dispersed in water applying high shear forces.

The lubricant suspension is poured into the EUDRAGIT® dispersion applying gentle stirring. Stirring is continued through the entire coating process.

Coating Process:
Drug layered pellets were coated with different coating suspensions in a fluidized bed apparatus under appropriate conditions, i.e. a spray rate of approximately 20 g/min coating suspension per kg cores and a bed temperature of approximately 25-28° C. After coating the pellets were fluidised at 50° C. for one hour in a fluid bed processor.

The compositions of the pellets is shown in Table 1. All amounts are given in %-weight/weight (w/w) on a dry basis.

TABLE 1

| Sr. No. | Ingredients | Example 1 | Example 2 | Example 3 | Example 4 | Comparative Example 5 |
|---|---|---|---|---|---|---|
| | Core | | | | | |
| 1. | Non pareil seeds | 14.56 | 15.40 | 14.56 | 15.40 | 14.04 |
| 2. | Sodium succinate (hexahydrate) | 18.90 | 19.99 | 18.90 | 19.99 | 18.22 |
| 3. | Povidone (PVP K 30) | 1.75 | 1.85 | 1.75 | 1.85 | 1.50 |
| 4. | Aerosil 200* | 0.46 | 0.49 | 0.46 | 0.49 | 0.45 |
| 5. | Phenylepherine Hydrochloride | 11.02 | 11.66 | 11.02 | 11.66 | 10.32 |
| | Coating | | | | | |
| 6. | Copolymer 1 | 31.51 | 33.33 | 31.51 | 33.33 | 31.58 |
| 7. | Copolymer 2 | 3.50 | 3.70 | 3.50 | 3.70 | 3.51 |
| 8. | Glyceryl monostearate | 1.75 | 1.85 | 1.75 | 1.85 | 1.75 |
| 9. | Triethyl citrate | 7.00 | 7.41 | 7.00 | 7.41 | 7.02 |
| 10. | Copolymer 3 | 9.55 | 4.32 | —.— | — — | — — |
| 11. | Copolymer 4 | —.— | —.— | 9.55 | 4.32 | — — |

*Aerosil 200 = colloidal silica, pharmaceutical quality, average particle size about 12 nm The results are summarized in Table 2.

TABLE 2

| Time in hr. | Example 1 | Example 2 | Example 3 | Example 4 | Example 5 comparative |
|---|---|---|---|---|---|
| 0.00 | 0.00 | 0.00 | 0.00 | 0.00 | 0.00 |
| 1.00 | 0.00 | 0.00 | 0.00 | 0.00 | 0.00 |
| 2.00 | 0.00 | 0.00 | 0.00 | 0.00 | 0.00 |
| 3.00 | 0.00 | 0.00 | 0.00 | 0.00 | 0.00 |
| 5.00 | 2.16 | 2.06 | 0.93 | 0.00 | 0.01 |
| 6.00 | 5.15 | 5.62 | 1.51 | 0.64 | 2.40 |
| 6.50 | 12.16 | 10.30 | 6.14 | 4.06 | 7.54 |
| 7.00 | 23.62 | 19.09 | 15.89 | 9.48 | 17.56 |
| 7.50 | 38.26 | 33.00 | 29.80 | 18.28 | 32.36 |
| 8.00 | 52.99 | 42.25 | 45.86 | 30.14 | 44.95 |
| 9.00 | 77.57 | 63.48 | 73.55 | 56.62 | 62.81 |
| 10.00 | 93.58 | 80.19 | 93.11 | 84.88 | 78.47 |

TABLE 2-continued

| Time in hr. | Example 1 | Example 2 | Example 3 | Example 4 | Example 5 comparative |
|---|---|---|---|---|---|
| 11.00 | 96.89 | 90.12 | 95.49 | 90.61 | 81.65 |
| 12.00 | 99.13 | 94.72 | 98.13 | 96.45 | 86.92 |

As can be seen from Table 2 the pharmaceutical preparations of Examples 1 to 4 according to the present invention result in a more than 90% (substantially complete) release of the pharmaceutically active components within 12 hours. Additionally the pulse phase in the inventive examples 1 to 4, starting at the first time with more than 5% release, is generally steeper than in the comparative example 5. In contrast thereto in the comparative formulation the pharmaceutically active component was not completely released even after 12 hours.

Pellets Compressed into Tablets

The pellets according to example 2 and comparative example 5 were compressed into tablets as follows: The excipients were sifted through a 40# sieve. The pellets were mixed with half of the quantities of magnesium stearate, Aerosil 200 and talc as given in table 3. This blend was further mixed with the amount of microcrystalline cellulose Avivel PH 102 (Bitte genau angeben was das ist) given in table 3. The remaining half of the Aerosil 200 and talc together with the amount of Ac-Di-So (Bitte angeben was das ist) as given in table 3 were added and mixed. Finally the remaining half of the magnesium stearate was added and mixed. The blend was compressed on an compression machine using 15×7 mm capsule shaped punches.

TABLE 3

| Sr. No | Ingredient | mg/tablet |
|---|---|---|
| 1. | Pellets | 287.5 |
| 2. | Avivel PH 102 | 247.24 |
| 3. | Ac-di-sol | 17.24 |
| 4. | Talc | 17.24 |
| 5. | Aerosil 200 | 2.86 |
| 6. | Magnesium stearate | 2.86 |
|  | Total | 575 |

The results are summarised in table 4.

TABLE 4

| Time in h | Pellets example 2 | Pellets example 5 (comparative) |
|---|---|---|
| 0.00 | 0.00 | 0.00 |
| 1.00 | 0.00 | 0.00 |
| 2.00 | 1.01 | 4.47 |
| 5.00 | 1.34 | 7.07 |
| 5.50 | 1.41 | 7.65 |
| 6.00 | 2.04 | 9.12 |
| 6.50 | 4.43 | 10.68 |
| 7.00 | 12.08 | 14.95 |
| 8.00 | 40.86 | 38.86 |
| 9.00 | 72.25 | 60.18 |
| 9.50 | 83.77 | 68.60 |
| 10.00 | 90.84 | 74.73 |
| 11.00 | 95.79 | 82.81 |

As can be seen from Table 4 the tablet containing the pharmaceutical preparation of Examples 2 according to the present invention results in a more than 90% (substantially complete) release of the pharmaceutically active components within 10 hours. In contrast thereto in the tablet containing the comparative formulation the pharmaceutically active component was not completely released even after 12 hours.

The invention claimed is:

1. A pharmaceutical or nutraceutical preparation having a sigmoidal release profile which releases more than 90% of its pharmaceutically or nutraceutically active components within 10 hours of oral administration, consisting essentially of:
    a) a core comprising a pharmaceutically or nutraceutically active substance and a substance that acts in a modulatory manner, during release of the pharmaceutically or nutraceutically active substance; and
    b) a single controlling layer surrounding the core comprising i) 55 to 92% by weight, based on a total weight of (meth)acrylic acid ester copolymers present in the layer, of first (meth)acrylic acid ester copolymers; and ii) 8 to 45% by weight, based on the total weight of (meth)acrylic acid ester copolymers present in the layer, of second (meth)acrylic acid ester copolymers;
        wherein said first (meth)acrylic acid ester copolymers comprise one or a mixture of a plurality of (meth)acrylate copolymers comprising 80 to less than 93% by weight, based on the total weight of the first (meth)acrylic acid ester copolymers, of structural units obtained from $C_1$ to $C_4$ alkyl esters of (meth)acrylic acid, and more than 7 to 20% by weight, based on the total weight of the first (meth)acrylic acid ester copolymers, of structural units obtained from (meth)acrylate monomers with a quaternary ammonium group in an alkyl radical; and
        wherein said second (meth)acrylic acid ester copolymers comprise one or a mixture of a plurality of (meth)acrylate copolymers comprising more than 5 but not more than 59% by weight, based on the total weight of the second (meth)acrylic acid ester copolymers, of structural units obtained from acrylic acid or (meth)acrylic acid.

2. The preparation according to claim 1, wherein the second (meth)acrylic acid ester copolymers comprise 7 to 59% by weight, based on the total weight of the second (meth)acrylic acid ester copolymers, of structural units obtained from acrylic acid or (meth)acrylic acid.

3. The preparation according to claim 1, wherein the second (meth)acrylic acid ester copolymers comprise 18 to 59% by weight, based on the total weight of the second (meth)acrylic acid ester copolymers, of structural units obtained from acrylic acid or (meth)acrylic acid.

4. The preparation according to claim 1, wherein the second (meth)acrylic acid ester copolymers comprise 40 to 59% by weight, based on the total weight of the second (meth)acrylic acid ester copolymers, of structural units obtained from acrylic acid or (meth)acrylic acid.

5. The preparation according to claim 1, wherein the second (meth)acrylic acid ester copolymers comprise 41 or more but less than 95% by weight, based on the total weight of the second (meth)acrylic acid ester copolymers, of structural units obtained from $C_1$ to $C_4$ alkyl esters of (meth)acrylic acid.

6. The preparation according to claim 1, wherein the second (meth)acrylic acid ester copolymers comprise 41 to 60% by weight, based on the total weight of the second (meth)acrylic acid ester copolymers, of structural units obtained from methyl (meth)acrylate or ethyl acrylate and 40 to 59% by weight, based on the total weight of the second (meth)acrylic acid ester copolymers, of structural units obtained from (meth)acrylic acid.

7. The preparation according to claim 1, wherein the first (meth)acrylic acid ester copolymers comprise (meth)acrylate copolymers comprising 80 to 90% by weight, based on the total weight of the first (meth)acrylic acid ester copolymers, of structural units obtained from $C_1$ to $C_4$ alkyl esters of (meth)acrylic acid and 10 to 20% by weight, based on the total weight of the first (meth)acrylic acid ester copolymers, of structural units obtained from (meth)acrylate monomers with a quaternary ammonium group in the alkyl radical.

8. The preparation according to claim 1, wherein the first (meth)acrylic acid ester copolymers comprise a mixture of
- 40 to 99% by weight, based on the total weight of the mixture, of a first submixture of (meth)acrylate copolymers comprising 93 to 98% by weight, based on the total weight of the first submixture, of (meth)acrylate copolymers of structural units obtained from $C_1$ to $C_4$ alkyl esters of (meth)acrylic acid, and 2 to 7% by weight, based on the total weight of the first submixture, of (meth)acrylate copolymers of structural units obtained from (meth)acrylate monomers with a quaternary ammonium group in the alkyl radical; and
- 1 to 60% by weight, based on the total weight of the mixture, of a second submixture of (meth)acrylate copolymers comprising 85 or more but less than 93% by weight, based on the total weight of the second submixture, of (meth)acrylate copolymers of structural units obtained from $C_1$ to $C_4$ alkyl esters of (meth)acrylic acid and more than 7 but no more than 15% by weight, based on the total weight of the second submixture, of (meth)acrylate copolymers of structural units obtained from (meth)acrylate monomers with a quaternary ammonium group in the alkyl radical.

9. The preparation according to claim 1, wherein the structural units comprising a quaternary ammonium group in the alkyl radical are obtained from trimethylammoniumethyl methacrylate chloride.

10. The preparation according to claim 1, wherein the controlling layer comprises i) 75 to 92% by weight, based on the total weight of (meth)acrylic acid ester copolymers present in the layer, of the first (meth)acrylic acid ester copolymers and ii) 8 to 25% by weight, based on the total weight of (meth)acrylic acid ester copolymers present in the layer, of the second (meth)acrylic acid ester copolymers.

11. The preparation according to claim 1, wherein the core is free of a controlling layer comprising a pharmaceutically acceptable polymer, wax, resin or protein and wherein no further controlling layer comprising a pharmaceutically acceptable polymer, wax, resin or protein is located between the core and the controlling layer b).

12. The preparation according to claim 1, wherein the substance that acts in a modulatory manner during the release of the pharmaceutically or nutraceutically active substance is selected from the group consisting of organic acids and salts of an organic acid.

13. The preparation according to claim 12, wherein the organic acids are selected from the group consisting of citric acid, fumaric acid, formic acid, acetic acid, maleic acid, succinic acid, tartaric acid, glutaric acid, lactic acid and mixtures thereof and the salts of the organic acid are selected from the group consisting of ammonium, lithium, sodium and potassium salts of said organic acids and mixtures thereof.

14. The preparation according to claim 1, wherein the substance that acts in a modulatory manner is sodium choride (NaCl).

15. A tablet comprising the pharmaceutical or nutraceutical preparation according to claim 1.

16. A gelatin or HPMC capsule comprising the pharmaceutical or nutraceutical preparation according to claim 1.

17. A process for increasing a release rate of a pharmaceutically or nutraceutically active substance in physiologically fluids in a sigmoidal release profile, consisting essentially of:
- preparing one or a mixture of a plurality of (meth)acrylate copolymers comprising more than 5 but no more than 59% by weight, based on the weight of the copolymers, of structural units obtained from acrylic acid or (meth)acrylic acid; and
- applying a single controlling layer to a core comprising the pharmaceutically or nutraceutically active substance and a substance that acts in a modulatory manner during the release of pharmaceutically or nutraceutically active substance;
- wherein said single controlling layer is applied to the core as a coating comprising: (1) said one or a mixture of a plurality of (meth)acrylate copolymers; and (2) one or a mixture of a plurality of other (meth)acrylate copolymers comprising (a) 80 to less than 93% by weight of other (meth)acrylic acid ester copolymers of structural units obtained from $C_1$ to $C_4$ alkyl esters of (meth)acrylic acid, and (b) more than 7 to 20% by weight of other (meth)acrylic acid ester copolymers of structural units obtained from (meth)acrylate monomers with a quaternary ammonium group in the alkyl radical.

18. The process according to claim 17, wherein the (1) one or a mixture of a plurality of (meth)acrylate copolymer(s) comprising structural units obtained from acrylic acid or (meth)acrylic acid is/are present in the controlling layer in an amount of 8 to 45% by weight and the (2) one or a mixture of a plurality of other (meth)acrylate copolymer(s) comprising a quaternary ammonium group is/are present in the controlling layer in an amount of 55 to 92% by weight; whereby the weight percentage is based on the total weight of (meth)acrylate copolymers present in the controlling layer.

19. The process according to claim 17, wherein the (1) one or a mixture of a plurality of (meth)acrylate copolymer(s) comprising structural units derived from acrylic acid or (meth)acrylic acid is/are present in the controlling layer in an amount of 8 to 25% by weight and the (2) one or a mixture of a plurality of other (meth)acrylate copolymer(s) comprising a quaternary ammonium group is/are present in the controlling layer in an amount of 75 to 92% by weight; whereby the weight percentage is based on the total weight of (meth)acrylate copolymers present in the controlling layer.

20. The process according to claim 17, wherein the coating further comprises one or a mixture of a plurality of other (meth)acrylate copolymer(s) comprising 93 to 98% by weight, based on the weight of the other (meth)acrylic acid ester copolymer(s), of structural units obtained from $C_1$ to $C_4$ alkyl esters of (meth)acrylic acid, and 2 to 7% by weight, based on the weight of the other (meth)acrylic acid ester copolymer(s), of structural units obtained from (meth)acrylate monomers with a quaternary ammonium group in the alkyl radical; and
- the substance that acts in a modulatory manner during the release of pharmaceutically active substance is selected from the group consisting of organic acids and salts of an organic acid.

* * * * *